(12) United States Patent
Li et al.

(10) Patent No.: US 10,628,971 B2
(45) Date of Patent: Apr. 21, 2020

(54) SAMPLING OF SCANNING DEVICE

(71) Applicant: Beijing Neusoft Medical Equipment Co., Ltd., Beijing (CN)

(72) Inventors: Shuangxue Li, Shenyang (CN); Liang Ren, Shenyang (CN); Shanshan Lou, Shenyang (CN)

(73) Assignee: Beijing Neusoft Medical Equipment Co., Ltd., Beijing (CN)

( * ) Notice: Subject to any disclaimer, the term of this patent is extended or adjusted under 35 U.S.C. 154(b) by 177 days.

(21) Appl. No.: 15/796,493

(22) Filed: Oct. 27, 2017

(65) Prior Publication Data

US 2018/0122107 A1    May 3, 2018

(51) Int. Cl.
*G06T 11/00* (2006.01)
*A61B 6/00* (2006.01)
*A61B 6/03* (2006.01)
*G01N 23/046* (2018.01)

(52) U.S. Cl.
CPC ............ *G06T 11/005* (2013.01); *A61B 6/032* (2013.01); *A61B 6/4233* (2013.01); *A61B 6/482* (2013.01); *A61B 6/54* (2013.01); *G01N 23/046* (2013.01); *G01N 2223/419* (2013.01); *G01N 2223/427* (2013.01)

(58) Field of Classification Search
None
See application file for complete search history.

(56) References Cited

U.S. PATENT DOCUMENTS

2003/0031289 A1*  2/2003  Hsieh ..................... A61B 6/032
378/4

* cited by examiner

*Primary Examiner* — Edwin C Gunberg
(74) *Attorney, Agent, or Firm* — McCoy Russell LLP

(57) ABSTRACT

The present disclosure provides a sampling method and sampling apparatus of a scanning device. In at least one example, the sampling method comprises acquiring a ray attenuation variation at each of a plurality of scanning angles of the scanning device, determining a corrected sampling interval at each of the scanning angles of the scanning device by adjusting an initial sampling interval at each of the scanning angles of the scanning device according to the ray attenuation variation at each of scanning angles, and performing actual sampling according to the corrected sampling interval at each of the scanning angles of the scanning device.

10 Claims, 7 Drawing Sheets

---

S101 — Acquire a ray attenuation variation at each of a plurality of scanning angles of the scanning device S102 — Adjust an initial sampling interval at each of the scanning angles according to the ray attenuation variation at each of the scanning angles so as to determine a corrected sampling interval at each of the scanning angles of the scanning device S103 — Perform actual sampling on a subject according to the corrected sampling interval at each of the scanning angles of the scanning device

SAMPLING OF SCANNING DEVICE

CROSS REFERENCE TO RELATED APPLICATIONS

This application claims priority to Chinese Patent Application No. 201610970248.X, entitled "SAMPLING OF SCANNING DEVICE," filed on Oct. 27, 2016, the entire contents of which are incorporated herein by reference for all purposes.

TECHNICAL FIELD

The present disclosure relates to sampling of a scanning device.

BACKGROUND

A scanning device may include a scanning system including a tube and a detector, etc. When the scanning device scans a subject, the scanning system may be rotated around a center of rotation, rays emitted from the tube may penetrate through the subject, and the detector may receive rays emitted from the tube and through the subject. In the scanning process, the scanning system may turn a circle or a plurality of circles to collect signals (the process of collecting signals also may be referred to as sampling), and then the scanning device may reconstruct an image according to the collected signals.

NEUSOFT MEDICAL SYSTEMS CO., LTD. (NMS), founded in 1998 with its world headquarters in China, is a leading supplier of medical equipment, medical IT solutions, and healthcare services. NMS supplies medical equipment with a wide portfolio, including CT, Magnetic Resonance Imaging (MRI), digital X-ray machine, ultrasound, Positron Emission Tomography (PET), Linear Accelerator (LINAC), and biochemistry analyser. Currently, NMS' products are exported to over 60 countries and regions around the globe, serving more than 5,000 renowned customers. NMS's latest successful developments, such as 128 Multi-Slice CT Scanner System, Superconducting MRI, LINAC, and PET products, have led China to become a global high-end medical equipment producer. As an integrated supplier with extensive experience in large medical equipment, NMS has been committed to the study of avoiding secondary potential harm caused by excessive X-ray irradiation to the subject during the CT scanning process.

DETAILED DESCRIPTION

When a scanning system scans a subject, a detector included in the scanning system may perform isochronous and equidistant sampling in a rotation process. In other words, scanning time and sampling angle interval between each two adjacent sampling points may be identical. When the sampling interval is larger, the scanning time may be relatively longer. Consequently, more ray photons may be received by the detector, noise of collected signals may be lower, but spatial resolution of a reconstructed image may be relatively reduced. On the contrary, when the sampling interval is smaller, the scanning time may be relatively shorter. Consequently, less ray photons may be received by the detector, noise of collected signals may be higher, but spatial resolution of a reconstructed image may be relatively increased.

Figure 1:
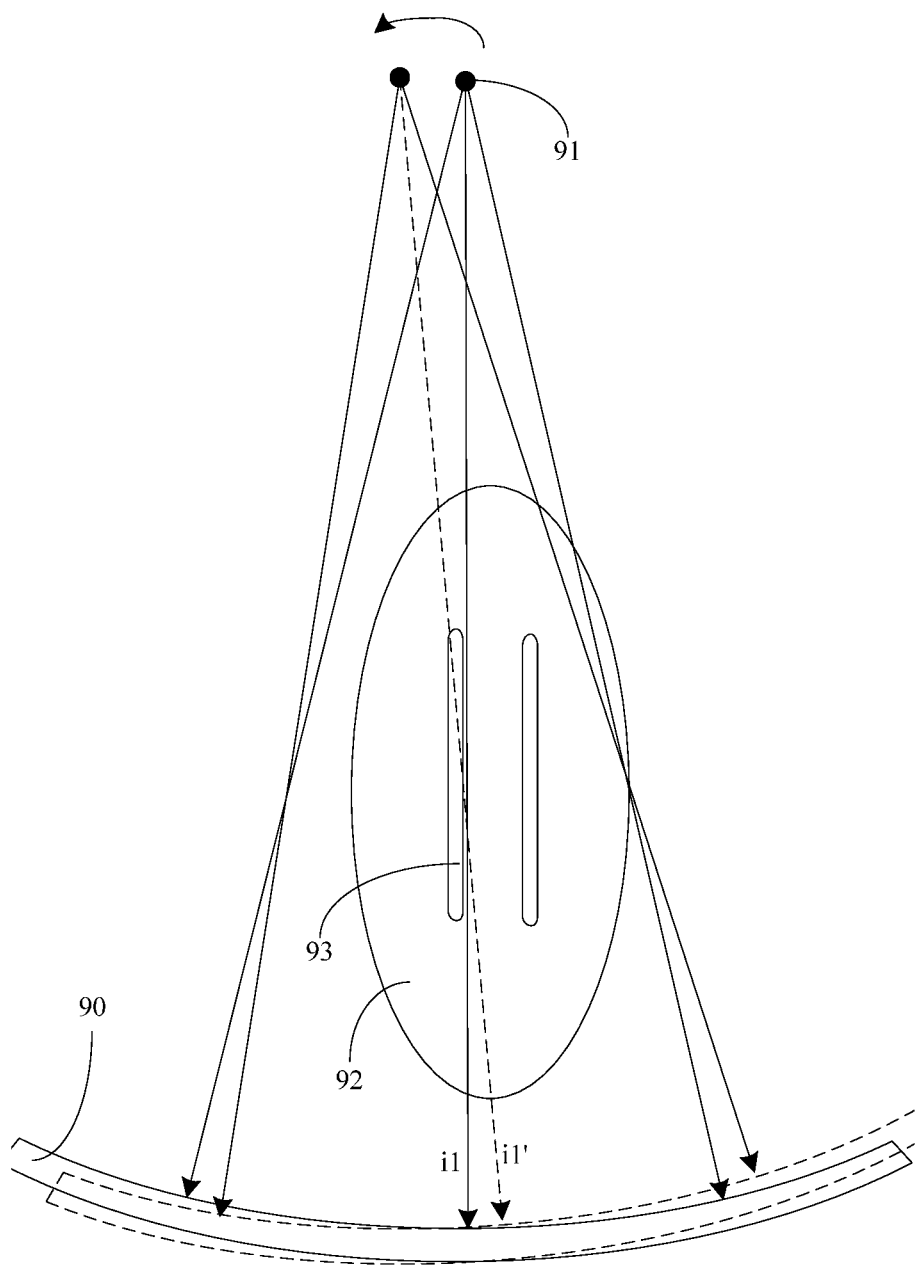
FIG. 1 is a schematic diagram illustrating an application scene where a scanning system scans a subject according to an example of the present disclosure.

FIG. 1 is a schematic diagram illustrating an application scene where a scanning system scans a subject according to an example of the present disclosure. In this scene, when the scanning system samples within a circumference, nearby some scanning angles, attenuation variation of ray penetrating through the subject may be relatively larger. For example, when a tube 91 and a detector 90 of the scanning system are rotated around a center of rotation (a direction of rotation is the reverse direction of arrow in FIG. 1), ray i1 after rotation may change to ray i1'. Compared with the ray i1, the ray i1' has larger attenuation variation. This is because the ray i1 does not penetrate through a skeleton 93 of the subject 92, whereas the ray i1' may penetrate a relatively larger distance in the skeleton 93 of the subject 92. The ray attenuation capability of the skeleton 93 may be obviously different from that of other parts (such as, soft tissues) nearby the skeleton 93. In this case, relatively higher spatial resolution may be required at these scanning angles.

Figure 2:
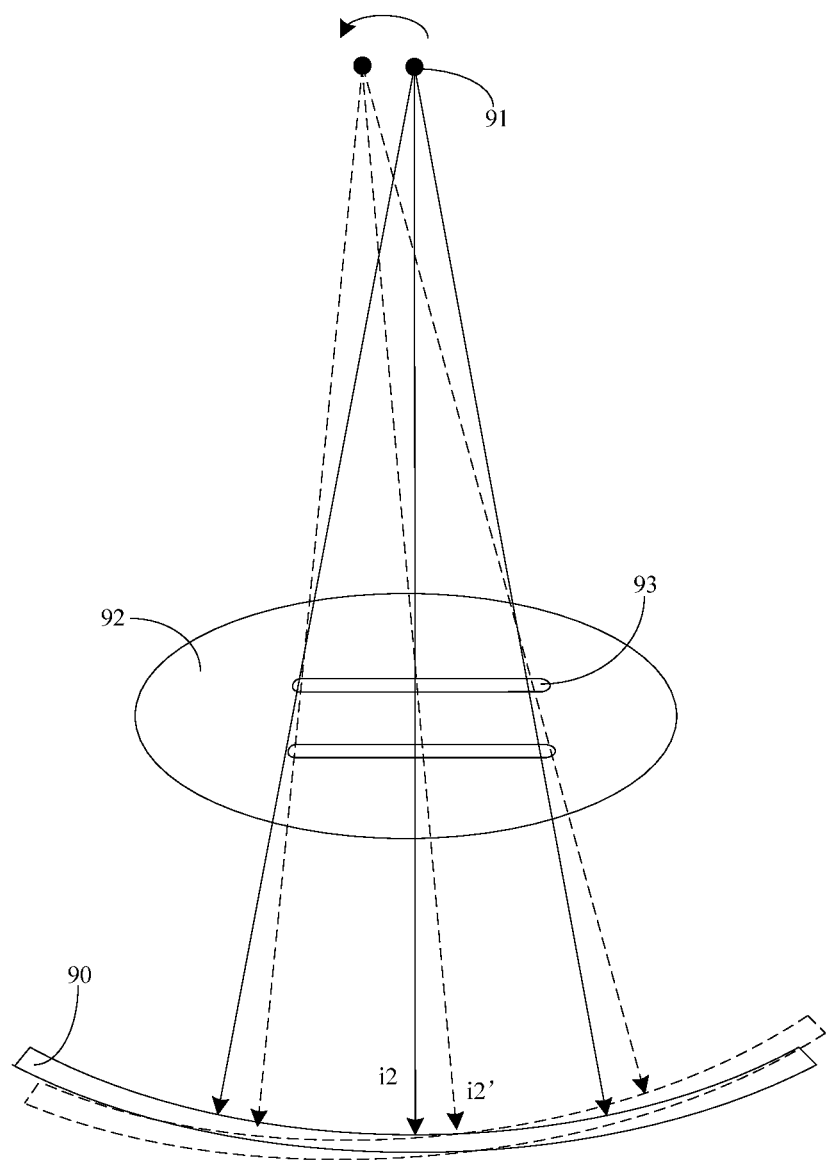
FIG. 2 is a schematic diagram illustrating an application scene where a scanning system scans a subject according to another example of the present disclosure.

FIG. 2 is a schematic diagram illustrating an application scene where a scanning system scans a subject according to another example of the present disclosure. In this scene, nearby some scanning angles, attenuation variation of rays penetrating through the subject may be relatively smaller. When the tube 91 and the detector 90 of the scanning system are rotated around the center of rotation, ray i2 after rotation may change to ray i2'. Compared with the ray i2, the ray i2' has basically identical attenuation variation. This is because variation of distance for the rays i2, i2' penetrating through the skeleton 93 and soft tissues of the subject 92 is relatively smaller. In this case, relatively lower spatial resolution may be okay at these scanning angles.

In an actual scanning process, relatively higher spatial resolution may be required at some scanning angles, or relatively lower spatial resolution may be required at other scanning angles. When isochronous and equidistant sampling is performed in the rotation process of the detector, specific requirements of respective scanning angles for the spatial resolution may be not satisfied. Thus, comprehensive performances of indicators, such as spatial resolution, scanning dose and so on may be poor.

Figure 3:
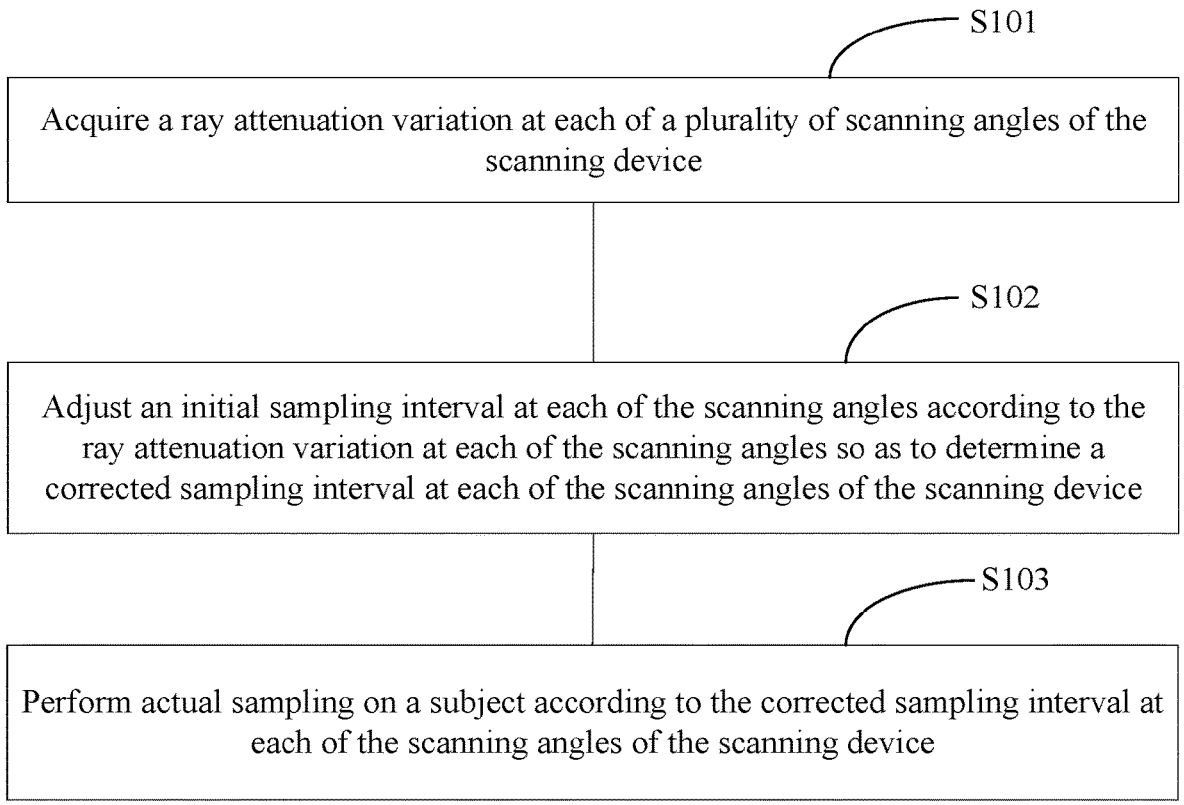
FIG. 3 is a schematic flow diagram of a sampling method of a scanning device according to an example of the present disclosure.

FIG. 3 is a schematic flow diagram of a sampling method of a scanning device according to an example of the present disclosure. The method may include blocks S101-S103.

At block S101, a ray attenuation variation at each of a plurality of scanning angles of the scanning device may be acquired.

At block S102, an initial sampling interval at each of the scanning angles may be adjusted according to the ray attenuation variation at each of the scanning angles so as to determine a corrected sampling interval at each of the scanning angles of the scanning device.

At block S103, actual sampling may be performed on a subject according to the corrected sampling interval at each of the scanning angles of the scanning device.

Figure 4:
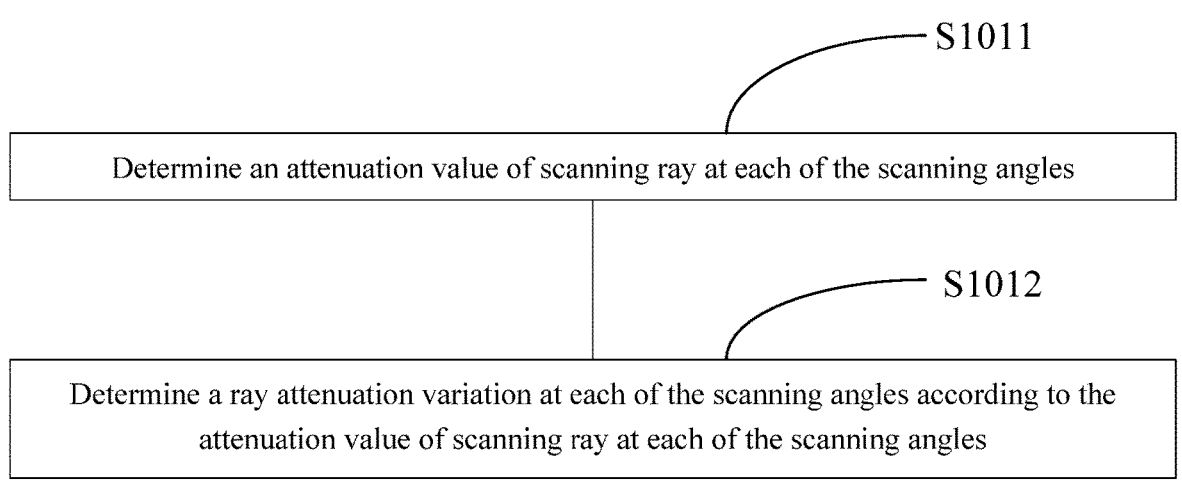
FIG. 4 is a detailed flowchart of block S101 in FIG. 3.

Referring to FIG. 4, block S101 may further include blocks S1011-S1012.

At block S1011, an attenuation value of scanning ray at each of the scanning angles may be determined.

At block S1012, a ray attenuation variation at each of the scanning angles may be determined according to the attenuation value of scanning ray at each of the scanning angles.

Figure 5:
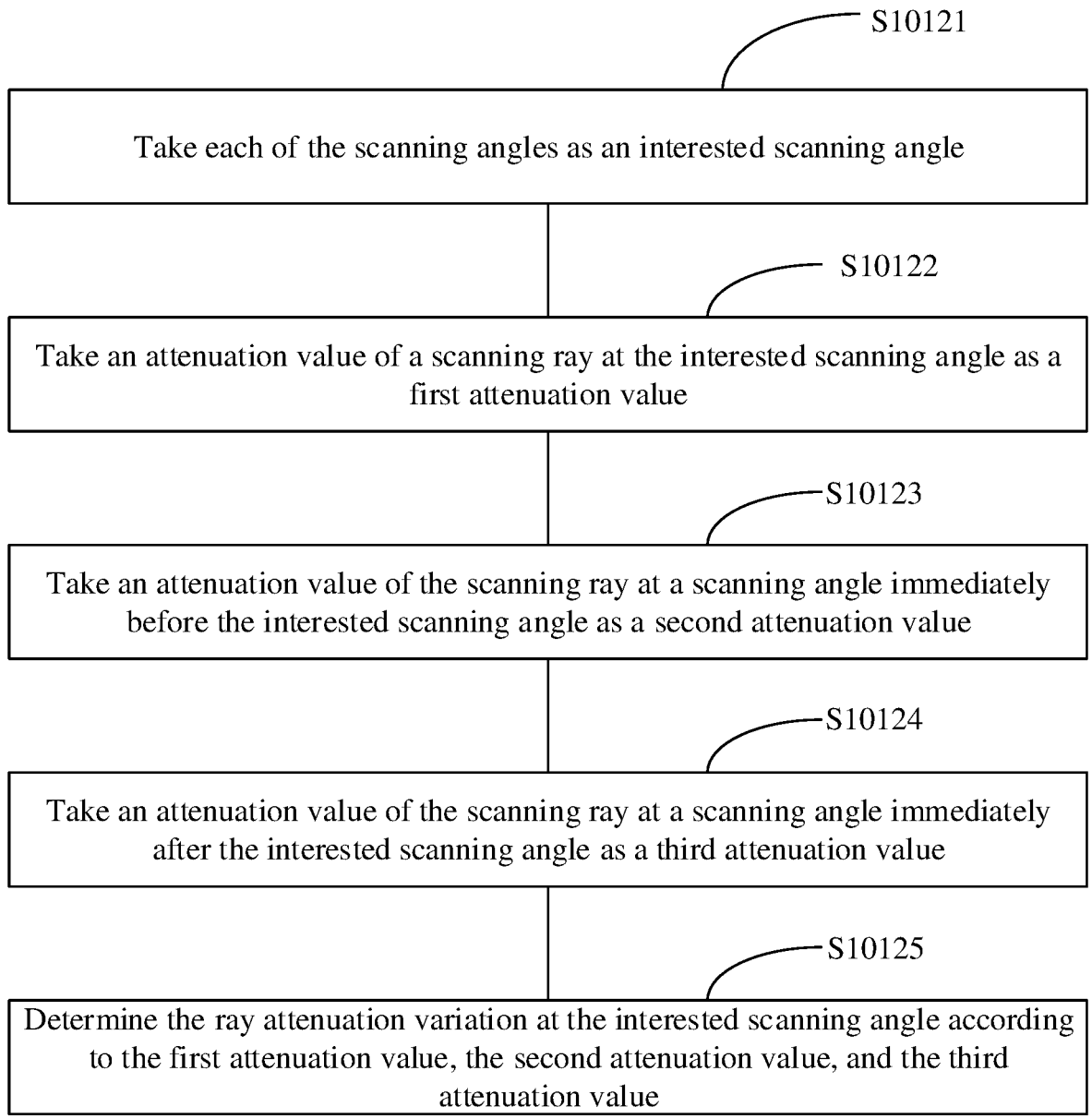
FIG. 5 is a detailed flowchart of block S1012 in FIG. 4.

Further referring to FIG. 5, block S1012 may further include blocks S10121-S10125.

At block S10121, each of the scanning angles is taken as an interested, or current, scanning angle.

At block S10122, an attenuation value of scanning ray at the interested scanning angle is taken as a first attenuation value.

At block S10123, an attenuation value of scanning ray at a scanning angle immediately before the interested scanning angle is taken as a second attenuation value.

At block S10124, an attenuation value of scanning ray at a scanning angle immediately after the interested scanning angle is taken as a third attenuation value.

At block S10125, the ray attenuation variation at the interested scanning angle is determined according to the first attenuation value, the second attenuation value, and the third attenuation value.

In an example, an absolute value of a difference between the first attenuation value and the second attenuation value may be denoted as a first attenuation value difference, and an absolute value of a difference between the first attenuation value and the third attenuation value may be denoted as a second attenuation value difference. The ray attenuation variation at the interested scanning angle may be a sum of the first attenuation value difference and the second attenuation value difference.

In an example, the block S102 may further include following blocks:

1) A threshold range $t_1$-$t_2$ of the ray attenuation variation at the scanning angle may be set, where $t_1$ is a lower threshold the threshold range, and $t_2$ is an upper threshold of the threshold range, and $t_1 < t_2$.

2) The initial sampling interval at the scanning angle of the scanning device may be increased when the ray attenuation variation at the scanning angle is smaller than the lower threshold $t_1$. In addition, to maintain the noise level of signals collected by the detector of the scanning device unchanged, the ray dose may also be correspondingly reduced.

3) The initial sampling interval at the scanning angle of the scanning device may be decreased when the ray attenuation variation at the scanning angle is greater than the upper threshold $t_2$. In addition, to maintain the noise level of signals collected by the detector of the scanning device unchanged, the ray dose may also be correspondingly increased.

4) The initial sampling interval at the scanning angle of the scanning device may be maintained unchanged when the ray attenuation variation at the scanning angle is between the lower threshold $t_1$ and the upper threshold $t_2$. In addition, to maintain the noise level of signals collected by the detector of the scanning device unchanged, the ray dose may also be unchanged.

According to the sampling method of the scanning device provided by the present disclosure, in an application scene, scanning angles of the scanning device in each circle of scanning process may be different. By adopting the above implementation, the initial sampling interval at each of the scanning angles of the scanning device may be adjusted according to the ray attenuation variation at the respective scanning angles to determine the corrected sampling interval at each of the scanning angles of the scanning device. Actual sampling may be performed on the subject according to the corrected sampling interval at each of the scanning angles of the scanning device. Real-time calculation and adjustment may be performed on the sampling interval and/or scanning dose in each circle of scanning process, so that a relatively reasonable sampling interval and/or scanning dose may be always employed for sampling in the whole sampling process. In this way, the comprehensive performances of indicators, such as the spatial resolution, the scanning dose, and so on may be optimized.

According to the sampling method of the scanning device provided by the present disclosure, in another application scene, the scanning angles of the scanning device in each circle of scanning process may be identical. The corrected sampling interval at each of the scanning angles in the first circle of scanning process may be first determined, then a fixed sampling scheme of the scanning device may be constructed with the corrected sampling interval at each of the scanning angles in the first circle of scanning process, and then the actual sampling may be performed according to the fixed sampling scheme in each circle of scanning process of the scanning device. In this application scene, the sampling method of the scanning device of the present disclosure may include the following blocks:

determining each of the scanning angles in the first circle of scanning process for the scanning device by performing a pre-scanning on the subject with a low scanning dose;

determining a ray attenuation variation at each of the scanning angles in the first circle of scanning process;

adjusting the initial sampling interval at each of the scanning angles of the scanning device in the first circle of scanning process according to the ray attenuation variation at each of the scanning angles in the first scanning process, so as to determine the corrected sampling interval at each of the scanning angles of the scanning device in the first circle of scanning process;

constructing a fixed sampling scheme of the scanning device with the corrected sampling interval at each of the scanning angles of the scanning device in the first circle of scanning process; and performing the actual sampling on the subject according to the fixed sampling scheme in each circle of scanning process of the scanning device.

According to the sampling method of the scanning device of the present disclosure, in this application scene, the corrected sampling interval at each of the scanning angles in the first circle of scanning process may be determined, then the fixed sampling scheme of the scanning device may be constructed with the corrected sampling interval at each of the scanning angles in the first circle of scanning process, and then the actual sampling may be performed on the subject according to the fixed sampling scheme in each circle of scanning process. Real-time calculation and adjustment of the sampling interval may be not required in the whole scanning process, but still a relatively reasonable sampling interval may be always employed for sampling in the whole sampling process. In this way, specific requirements of each of the scanning angles for the spatial resolution may be satisfied, and the comprehensive performances of indicators, such as the spatial resolution, the scanning dose, and so on may be optimized. In addition, to maintain the noise level of signals collected by the detector of the scanning device unchanged, the scanning dose may be correspondingly decreased, increased, or maintained.

In an example, the scanning device may include a plurality of channels for scanning (hereinafter referred to as channels or interested channels). In this application scene, determining the attenuation value of scanning ray at each of the scanning angles may include: determining an attenuation value of scanning ray at each of the scanning angles with respect to a ray beam emitted from each of the plurality of channels. In an example, the above block S1011 may further include: determining the attenuation value of scanning ray at the scanning angle with respect to the ray beam emitted from the channel according to the respective attenuation values of scanning ray at a scanned angle with respect to the ray beam emitted from each of the plurality of channels.

In other words, the attenuation value of scanning ray at the scanning angle with respect to the ray beam emitted from the channel may be estimated according to the attenuation value of scanning ray at the scanned angle with respect to the ray beam emitted from the channel, then the ray attenuation variation at the scanning angle may be determined, and then the corrected sampling interval at the scanning angle of the scanning device may be determined by adjusting the initial sampling interval at the scanning angle of the scanning device. When actually scanning, at the scanning angle, the scanning device may sample according to the determined corrected sampling interval.

The sampling method of the scanning device of the present disclosure may be described in detail according to an example.

Figure 6:
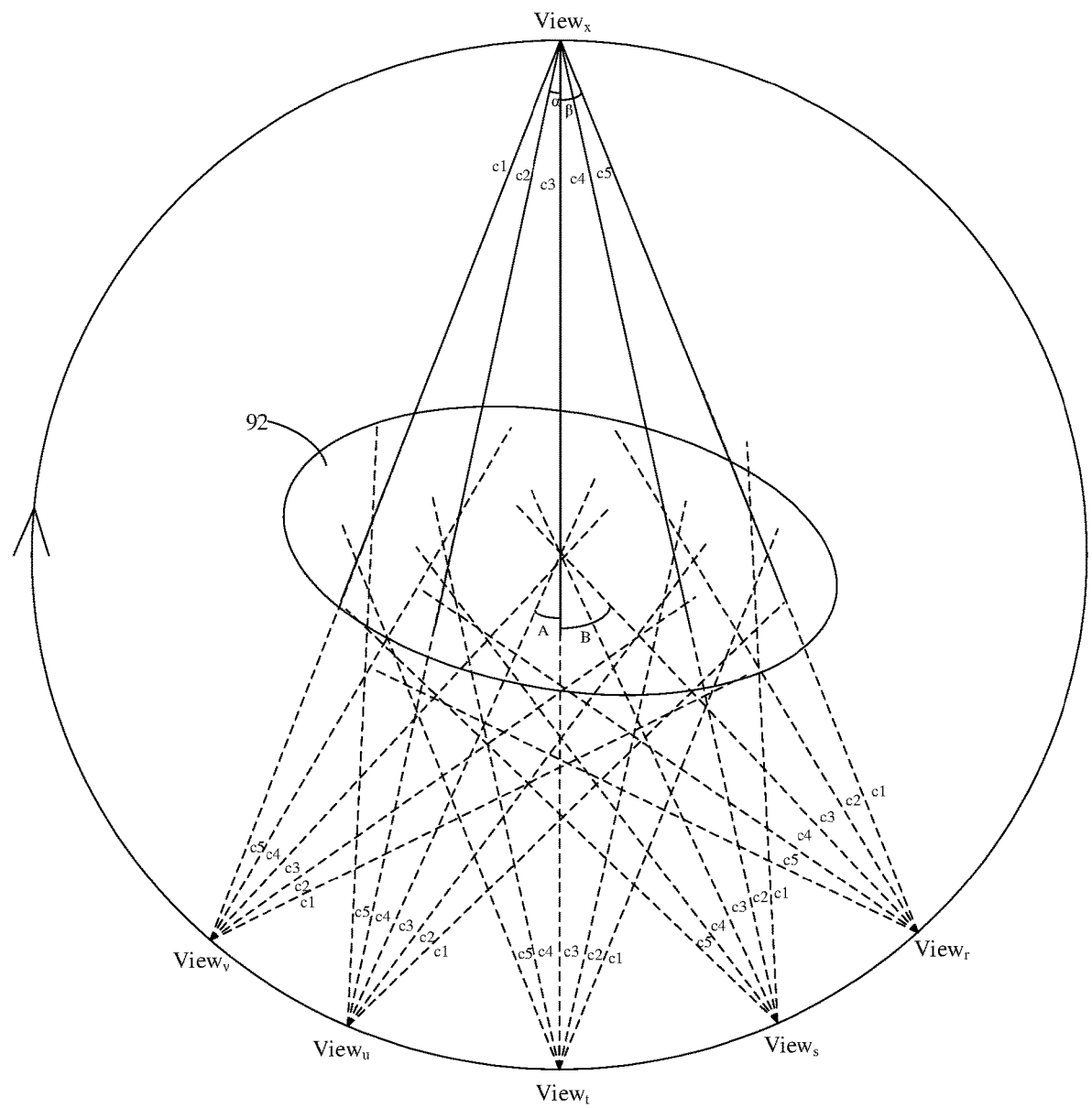
FIG. 6 is a schematic diagram of a sampling method of a scanning device according to an example of the present disclosure.

FIG. 6 is a schematic diagram of a sampling method of a scanning device according to an example of the present disclosure. In this example, the scanning device may include five channels c1~c5. The direction of rotation of the scanning device for scanning may be as shown in the direction of arrow in FIG. 6. It is assumed that the respective scanning angle corresponding to positions $View_r$, $View_s$, $View_t$, $View_u$ and $View_v$ in FIG. 6 are the scanned angle and the scanning angle corresponding to the position $View_x$ is a to-be-scanned angle.

1) The attenuation value of scanning ray at the to-be-scanned angle (e.g., the scanning angle corresponding to the position $View_x$) with respect to the ray beam emitted from each of the channels may be determined according to the attenuation value of scanning ray at the scanned angles (e.g., the respective scanning angle corresponding to the positions $View_r$, $View_s$, $View_t$, $View_u$ and $View_v$) with respect to the ray emitted from each of the channels.

According to a principle that the attenuation values of two ray beams, penetrating through a subject, which are in the same straight line, may be equal, the attenuation value of scanning ray at the scanning angle $View_v$ with respect to the ray beam emitted from the channel c5 may be determined as the attenuation value of scanning ray at the scanning angle $View_x$ with respect to the ray beam emitted from the channel c1; the attenuation value of scanning ray at the scanning angle $View_u$ with respect to the ray beam emitted from the channel c4 may be determined as the attenuation value of scanning ray at the scanning angle $View_x$ with respect to the ray beam emitted from the channel c2; the attenuation value of scanning ray at the scanning angle $View_t$ with respect to the ray beam emitted from the channel c3 may be determined as the attenuation value of scanning ray at the scanning angle $View_x$ with respect to the ray beam emitted from the channel c3; the attenuation value of scanning ray at the scanning angle $View_s$ with respect to the ray beam emitted from the channel c2 may be determined as the attenuation value of scanning ray at the scanning angle $View_x$ with respect to the ray beam emitted from the channel c4; and the attenuation value of scanning ray at the scanning angle $View_r$ with respect to the ray beam emitted from the channel c1 may be determined as the attenuation value of scanning ray at the scanning angle $View_x$ with respect to the ray beam emitted from the channel c5. Five ray beams at the scanning angle $View_x$ may be emitted from each of the channels c1 through c5 inclusive. The scanned angles (such as $View_r$, $View_s$, $View_t$, $View_u$ and $View_v$) corresponding to the ray beams, which are in the straight line with these five ray beams respectively, may be acquired relatively easily. For example, the positions of the scanned angles $View_u$ and $View_r$ corresponding to the channels c2, c5 at the scanning angle $View_x$ may be 180°−A and 180°+B respectively, where the angles A, B respectively are 2×α and 2×β, α is an included angle between the channel c2 and a central channel, and β is an included angle between the channel c5 and the central channel. In this way, because the attenuation value of the scanning ray at the scanning angles with respect to the ray beam emitted from each of the channels is known, the attenuation values of scanning ray at the scanning angle $View_x$ with respect to the ray beams emitted from the five channels at the scanning angle may be determined.

As can be seen from FIG. 6, assuming sequences for determining the attenuation values of the ray beams emitted from the five channels at the scanning angle $View_x$ may be as below: c5→c4→c3→c2→c1. After the attenuation value of scanning ray at the scanning angle $View_x$ with respect to the ray beam emitted from the channel c1 is determined, it may be considered that all the attenuation values of the ray beams emitted from the five channels at the scanning angle $View_x$ are determined. At this time, the scanning angle $View_x$ is a new scanned angle. In this way, an attenuation value of scanning ray at a next to-be-scanned angle with respect to the ray beam emitted from each of the channels may be determined according to the attenuation value of scanning ray at the scanned angle with respect to the ray beam emitted from each of the channels. It may be known when the attenuation values of the ray beams emitted from the five channels at the scanning angle $View_x$ may be obtained. After sampling at the scanning angle $View_x$ is completed, sampling at a next to-be-scanning angle may be proceeded.

2) Determining the ray attenuation variation at the scanning angle $View_x$ may include as below.

2.1. Each of the five channels is taken as an interested channel. A first attenuation value difference for the interested channel is obtained according to an absolute value of a difference between the attenuation value of scanning ray at the scanning angle $View_x$ with respect to the ray beam emitted from the interested channel and the attenuation value of scanning ray at a scanning angle immediately before the scanning angle (denoted by $View_{x-1}$) with respect to the ray beam emitted from the interested channel. A first difference set is constructed with the first attenuation value difference for each of the interested channels.

The first attenuation value difference may be represented by formula (1):

$$\Delta\text{diff}^1_i = |\text{diff}_{i,\ View(x)} - \text{diff}_{i,\ View(x-1)}|  \quad \text{formula (1)}.$$

The $\Delta\text{diff}^1_i$ may represent the first attenuation value difference of an $i^{th}$ channel. Values of i may be any integer from 1 to 5 inclusive. The $\text{diff}_{i,\ View(x)}$ may represent the attenuation value of scanning ray at the scanning angle $View_x$ with respect to the ray beam emitted from the $i^{th}$ channel. The $\text{diff}_{i,\ View(x-1)}$ may represent the attenuation value of scanning ray at the scanning angle $View_{x-1}$, with respect to the ray beam emitted from the $i^{th}$ channel. In this way, five first attenuation value differences may be obtained, and the five first attenuation value differences may be formed into the first difference set.

2.2. A second attenuation value difference for the interested channel is obtained according to an absolute value of a difference between the attenuation value of scanning ray at the scanning angle with respect to the ray beam emitted from the interested channel and the attenuation value of scanning ray at a scanning angle immediately after the scanning angle (denoted by $View_{x+1}$) with respect to the ray beam emitted from the interested channel. A second difference set is constructed with the second attenuation value difference for each of the interested channels.

The second attenuation value difference may be represented by formula (2):

$$\Delta\text{diff}^2_i = |\text{diff}_{i,\ View(x+1)} - \text{diff}_{i,\ View(x)}|  \quad \text{formula (2)}.$$

The $\Delta\text{diff}^2_i$ may represent the second attenuation value difference of the $i^{th}$ channel. Values of i may be any integer from 1 to 5 inclusive. The $\text{diff}_{i,\ View(x)}$ may represent the attenuation value of scanning ray at the scanning angle $View_x$ with respect to the ray beam emitted from the $i^{th}$ channel. The $\text{diff}_{i,\ view(x+1)}$ may represent the attenuation value of scanning ray at the scanning angle $View_{x+1}$ with respect to the ray beam emitted from the $i^{th}$ channel. In this way, five second attenuation value differences may be obtained, and the five second attenuation value differences may be formed into the second difference set.

2.3. The first attenuation value difference and the second attenuation value difference for the interested channel are summed to obtain an attenuation value difference sum for the interested channel. In this way, five attenuation value difference sums for the five channels can be obtained.

2.4. A maximum value is selected from the obtained five attenuation value difference sums as the ray attenuation variation at the scanning angle $View_x$. Assuming that the ray attenuation variation is denoted by Diff, the ray attenuation variation at the scanning angle $View_x$ may be represented by formula (3):

$$\text{Diff} = \text{Max}(\Delta\text{diff}^1_i + \Delta\text{diff}^2_i)  \quad \text{formula (3)}.$$

3) Setting the threshold range of the ray attenuation variation at the scanning angle $View_x$ may include:

3.1. An attenuation value difference group is constructed with the five first attenuation value differences in the first difference set and the five second attenuation value differences.

3.2. The minimum value $t_1$ and the maximum value $t_2$ from the attenuation value difference group are selected as the threshold range, that is, $t_1$ is the lower threshold of the threshold range, and $t_2$ is the upper threshold of the threshold range.

The initial sampling interval at the scanning angle $View_x$ of the scanning device may be increased when the ray attenuation variation at the scanning angle $View_x$ is less than or equal to the lower threshold (e.g., $\text{Diff} \leq t_1$).

The initial sampling interval at the scanning angle $View_x$ of the scanning device may be decreased when the ray attenuation variation at the scanning angle $View_x$ is great than or equal to the upper threshold (e.g., $\text{Diff} \geq t_2$).

The initial sampling interval at the scanning angle $View_x$ of the scanning device may be maintained unchanged when the ray attenuation variation at the scanning angle $View_x$ is between the lower threshold and the upper threshold (e.g., $t_1 \leq \text{Diff} \leq t_2$).

Corresponding to the examples of the sampling method of the scanning device according to the present disclosure, the present disclosure further provides a sampling apparatus of a scanning device.

Figure 7:
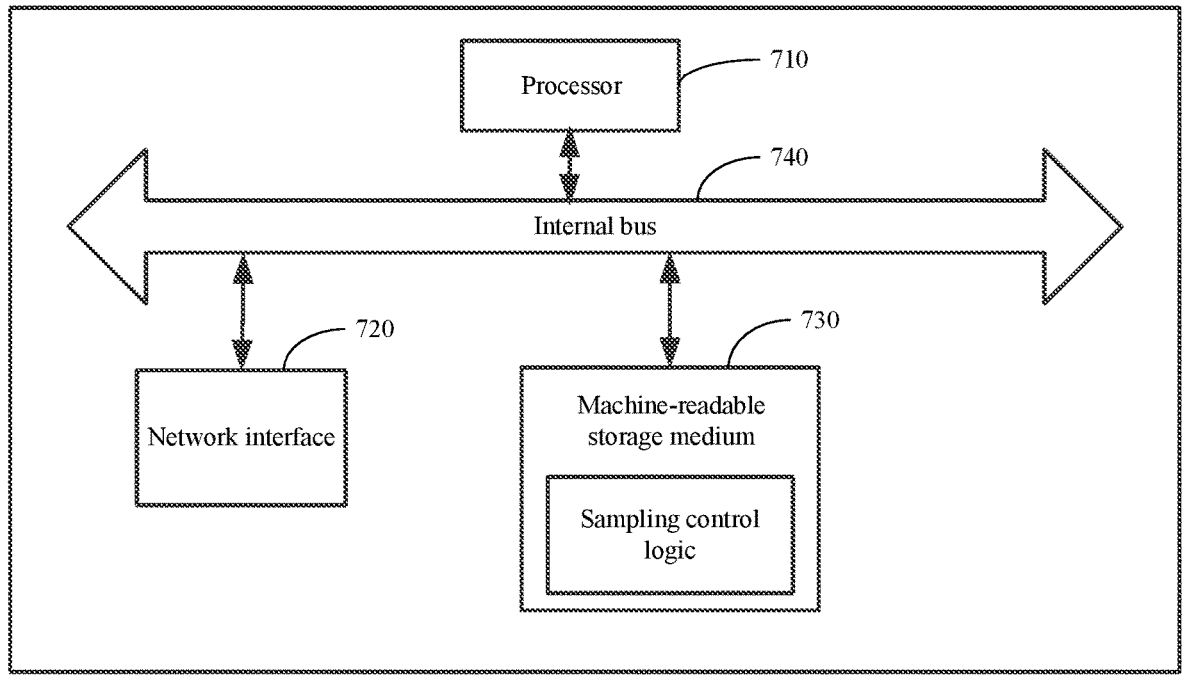
FIG. 7 is a hardware structure diagram of a sampling apparatus of a scanning device according to an example of the present disclosure.

FIG. 7 is a hardware structure diagram of a sampling apparatus of a scanning device according to an example of the present disclosure. The sampling apparatus of the scanning device may be implemented by software, or may be implemented by hardware or combination of software and hardware. In terms of hardware, in addition to a processor 710, a network interface 720, a machine-readable storage medium 730 and an internal bus 740 as shown in FIG. 7, the sampling apparatus of the scanning device may further include other hardwares based on actual functions, and further details are omitted for brevity.

In different examples, the machine readable storage medium 730 may be a read-only memory (ROM), a volatile memory, a non-volatile memory, a flash memory, a memory drive (such as a hard disk drive), a solid state drive, any type of memory disks (such as an optical disk or a DVD and so on), or similar storage medium or a combination thereof.

Figure 8:
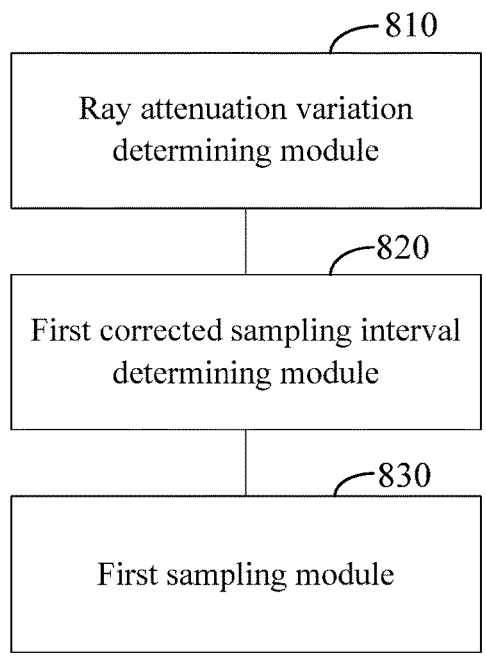
FIG. 8 is a function module diagram of sampling control logic of a scanning device according to an example of the present disclosure.

Further, the machine-readable storage medium 730 may store sampling control logic of the scanning device. As shown in FIG. 8, functionally divided, the control logic may include: a ray attenuation variation determining module 810, a first corrected sampling interval determining module 820, and a first sampling module 830.

The ray attenuation variation determining module 810 is configured to acquire a ray attenuation variation at each of a plurality of scanning angles of the scanning device.

The first corrected sampling interval determining module 820 is configured to determine a corrected sampling interval at each of the scanning angles of the scanning device by adjusting an initial sampling interval at each of the scanning angles of the scanning device according to the ray attenuation variation at each of the scanning angles.

The first sampling module 830 is configured to perform actual sampling on a subject according to the corrected sampling interval at each of the scanning angles of the scanning device.

Figure 9:
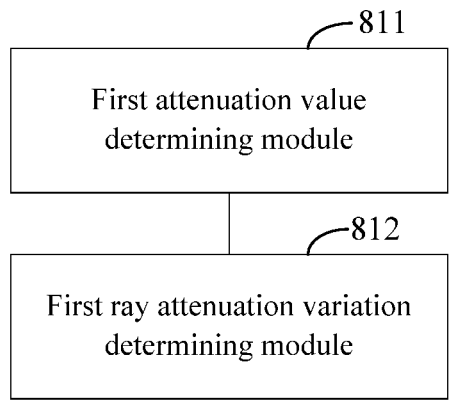
FIG. 9 is a function module diagram of a ray attenuation variation determining module according to an example of the present disclosure.

Referring to FIG. 9, a function module diagram of the ray attenuation variation determining module is illustrated according to an example of the present disclosure. The ray attenuation variation determining module 810 may further include a first attenuation value determining module 811 and a first ray attenuation variation determining module 812.

The first attenuation value determining module 811 is configured to determine an attenuation value of scanning ray at each of the scanning angles.

The first ray attenuation variation determining module 812 is configured to determine a ray attenuation variation at each of the scanning angles according to the attenuation value of scanning ray at each of the scanning angles.

Figure 10:
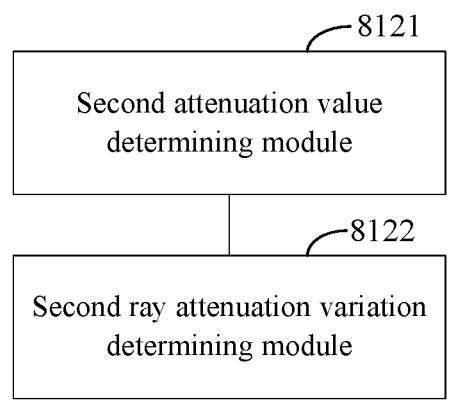
FIG. 10 is a function module diagram of a first ray attenuation variation determining module according to an example of the present disclosure.

Referring to FIG. 10, a function module diagram of the first ray attenuation variation determining module is illustrated according to an example of the present disclosure. The first ray attenuation variation determining module 812 may include: a second attenuation value determining module 8121 and a second ray attenuation variation determining module 8122.

The second attenuation value determining module 8121 is configured to take each of the scanning angles as an interested scanning angle, take an attenuation value of scanning ray at the interested scanning angle as a first attenuation value, take an attenuation value of scanning ray at a scanning angle immediately before the interested scanning angle as a second attenuation value, and take an attenuation value of scanning ray at a scanning angle immediately after the interested scanning angle as a third attenuation value.

The second ray attenuation variation determining module 8122 is configured to determine the ray attenuation variation at the interested scanning angle according to the first attenuation value, the second attenuation value, and the third attenuation value.

Figure 11:
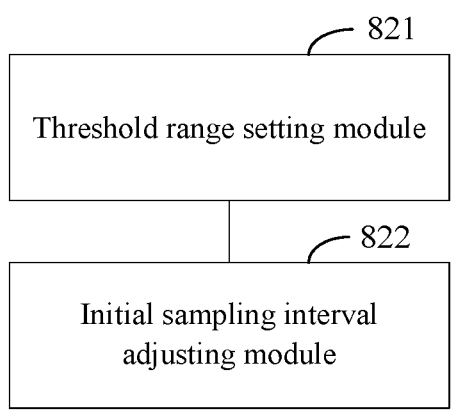
FIG. 11 is a function module diagram of a first corrected sampling interval determining module according to an example of the present disclosure.

Referring to FIG. 11, a function module diagram of a first corrected sampling interval determining module is illustrated according to an example of the present disclosure. The first corrected sampling interval determining module 820 may include: a threshold range setting module 821 and an initial sampling interval adjusting module 822.

The threshold range setting module 821 is configured to set a threshold range of the ray attenuation variation at the scanning angle, the threshold range including a lower threshold and an upper threshold.

The initial sampling interval adjusting module 822 is configured to:

increase the initial sampling interval at the scanning angle of the scanning device when the ray attenuation variation at the scanning angle is smaller than the lower threshold;

decrease the initial sampling interval at the scanning angle of the scanning device when the ray attenuation variation at the scanning angle is greater than the upper threshold; and maintain the initial sampling interval at the scanning angle of the scanning device unchanged when the ray attenuation variation at the scanning angle is between the lower threshold and the upper threshold.

In an example, the scanning device may include a plurality of channels for scanning, and the first attenuation value determining module 811 may be further configured to determine an attenuation variation value of scanning ray at each of the scanning angles with respect to a ray beam emitted from each of a plurality of channels comprised in the scanning device.

In an example, the first attenuation value determining module 811 may be further configured to determine the attenuation value of scanning ray at the scanning angle with respect to the ray beam emitted from the channel according to the respective attenuation values of scanning ray at a scanned angle with respect to the ray beam emitted from each of the plurality of channels.

In an example, the scanning angles in each circle of scanning process for the scanning device are the same, and the sampling control logic may further include: a pre-scanning module, a third ray attenuation variation determining module, a second corrected sampling interval determining module and a second sampling module.

The pre-scanning module is configured to determine each of the scanning angles in a first circle of scanning process for the scanning device by performing a pre-scanning on the subject with the scanning device.

The third ray attenuation variation determining module is configured to determine the ray attenuation variation at each of the scanning angles in the first circle of scanning process.

The second corrected sampling interval determining module is configured to determine the corrected sampling interval at each of the scanning angles of the scanning device in the first circle of scanning process by adjusting the initial sampling interval at each of the scanning angles of the scanning device in the first circle of scanning process according to the ray attenuation variation at each of the scanning angles in the first circle of scanning process.

The second sampling module is configured to construct a fixed sampling scheme of the scanning device with the corrected sampling interval at each of the scanning angles of the scanning device in the first circle of scanning process, and perform the actual sampling on the subject according to the fixed sampling scheme in each circle of scanning process of the scanning device.

The implementation processes of the functions and effects of each module in the above logic is described in detail in the implementation processes of the corresponding steps in the above method, and further description is omitted for brevity.

Taking the software implementation as an example, it is further described that how the sampling apparatus of the scanning device runs the sampling control logic. In this example, the sampling control logic of the present disclosure should be understood as machine-executable instructions stored in the machine-readable storage medium 730. When the processor 710 on the sampling apparatus of the scanning device of the present disclosure executes the sampling control logic, the processor 710 may be caused to execute the above sampling method by invoking the machine-executable instructions corresponding to the sampling control logic stored on the machine-readable storage medium 730.

For simplicity and illustrative purposes, the present disclosure is described by referring mainly to examples thereof. In the above descriptions, numerous specific details are set forth in order to provide a thorough understanding of the present disclosure. It will be readily apparent however, that the present disclosure may be practiced without limitation to these specific details. In other instances, some methods and structures have not been described in detail so as not to unnecessarily obscure the present disclosure. As used herein, the terms "a" and "an" are intended to denote at least one of a particular element, the term "includes" means includes but not limited to, the term "including" means including but not limited to, and the term "based on" means based at least in part on.

The above description merely provides examples of the present disclosure and is not intended to limit the present disclosure in any form. Although the present disclosure is disclosed by the above examples, the examples are not intended to limit the present disclosure. Those skilled in the art, without departing from the scope of the technical scheme of the present disclosure, may make a plurality of changes and modifications of the technical scheme of the present disclosure by the method and technical content disclosed above.

Therefore, without departing from the scope of the technical scheme of the present disclosure, based on technical essences of the present disclosure, any simple alterations, equal changes and modifications should fall within the protection scope of the technical scheme of the present disclosure. Accordingly, other examples are within the scope of the following claims.

The invention claimed is:

1. A sampling method of a scanning device, comprising:
acquiring a ray attenuation variation at each of a plurality of scanning angles of the scanning device;
determining a corrected sampling interval at each of the scanning angles of the scanning device by adjusting an initial sampling interval at each of the scanning angles of the scanning device according to the ray attenuation variation at each of the scanning angles; and
performing actual sampling on a subject according to the corrected sampling interval at each of the scanning angles of the scanning device;
wherein acquiring the ray attenuation variation at each of the plurality of scanning angles of the scanning device comprises:
determining an attenuation value of a scanning ray at each of the scanning angles; and
determining a ray attenuation variation at each of the scanning angles according to the attenuation value of the scanning ray at each of the scanning angles;
wherein determining the ray attenuation variation at each of the scanning angles according to the attenuation value of the scanning ray at each of the scanning angles comprises:
taking each of the scanning angles as an interested scanning angle;
taking the attenuation value of the scanning ray at the interested scanning angle as a first attenuation value;
taking an attenuation value of the scanning ray at a scanning angle immediately before the interested scanning angle as a second attenuation value;
taking an attenuation value of the scanning ray at a scanning angle immediately after the interested scanning angle as a third attenuation value;
determining an absolute value of a difference between the first attenuation value and the second attenuation value as a first attenuation value difference;
determining an absolute value of a difference between the first attenuation value and the third attenuation value as a second attenuation value difference; and
determining a sum of the first attenuation value difference and the second attenuation value difference as the ray attenuation variation at the interested scanning angle.

2. The method according to claim 1, wherein adjusting the initial sampling interval at the scanning angle of the scanning device comprises: setting a lower threshold and an upper threshold of the ray attenuation variation at the scanning angle of the scanning device; increasing the initial sampling interval at the scanning angle of the scanning device when the ray attenuation variation at the scanning angle is smaller than the lower threshold; decreasing the initial sampling interval at the scanning angle of the scanning device when the ray attenuation variation at the scanning angle is greater than the upper threshold; and maintaining the initial sampling interval at the scanning angle of the scanning device unchanged when the ray attenuation variation at the scanning angle is between the lower threshold and the upper threshold.

3. The method according to claim 2, further comprising:
determining each of the scanning angles in a first circle of a scanning process for the scanning device by performing a pre-scanning on the subject with the scanning device;
determining the ray attenuation variation at each of the scanning angles in the first circle of the scanning process;
determining the corrected sampling interval at each of the scanning angles of the scanning device in the first circle of the scanning process by adjusting the initial sampling interval at each of the scanning angles of the scanning device in the first circle of the scanning process according to the ray attenuation variation at each of the scanning angles in the first circle of the scanning process;
constructing a fixed sampling scheme of the scanning device with the corrected sampling interval at each of the scanning angles of the scanning device in the first circle of the scanning process; and
performing the actual sampling on the subject according to the fixed sampling scheme in each circle of the scanning process of the scanning device.

4. A sampling method of a scanning device, comprising:
determining an attenuation value of a scanning ray at each of a plurality of scanning angles with respect to a ray beam emitted from each of a plurality of channels comprised in the scanning device;
determining a ray attenuation variation at each of the scanning angles according to the attenuation value of the scanning ray at each of the scanning angles;
determining a corrected sampling interval at each of the scanning angles of the scanning device by adjusting an initial sampling interval at each of the scanning angles of the scanning device according to the ray attenuation variation at each of the scanning angles; and
performing actual sampling on a subject according to the corrected sampling interval at each of the scanning angles of the scanning device;
wherein determining the attenuation value of the scanning ray at the scanning angle with respect to the ray beam emitted from a channel comprises:
determining the attenuation value of the scanning ray at the scanning angle with respect to the ray beam emitted from the channel according to the respective attenuation values of the scanning ray at a scanned angle with respect to the ray beam emitted from each of the plurality of channels;
wherein determining the ray attenuation variation at the scanning angle comprises:
taking each of the plurality of channels as an interested channel, and
obtaining a first attenuation value difference for the interested channel according to an absolute value of a difference between the attenuation value of the scanning ray at the scanning angle with respect to the ray beam emitted from the interested channel and the attenuation value of the scanning ray at a scanning angle immediately before the scanning angle with respect to the ray beam emitted from the interested channel;
obtaining a second attenuation value difference for the interested channel according to an absolute value of a difference between the attenuation value of the scanning ray at the scanning angle with respect to the ray beam emitted from the interested channel and the attenuation value of the scanning ray at a scanning angle immediately after the scanning angle with respect to the ray beam emitted from the interested channel;
obtaining an attenuation value difference sum for the interested channel by summing the first attenuation value difference and the second attenuation value difference for the interested channel; and selecting a maximum value from the respective attenuation value difference sums for the plurality of channels as the ray attenuation variation at the scanning angle.

5. The method according to claim 4, wherein setting a lower threshold and an upper threshold of the ray attenuation variation at the scanning angle comprises:
constructing an attenuation value difference group with the respective first attenuation value differences for the plurality of channels and the respective second attenuation value differences for the plurality of channels;
selecting a minimum value from the attenuation value difference group as the lower threshold of the ray attenuation variation at the scanning angle; and
selecting a maximum value from the attenuation value difference group as the upper threshold of the ray attenuation variation at the scanning angle.

6. A sampling apparatus of a scanning device, the device comprising:
a processor and a machine-readable storage medium,
wherein by invoking and executing machine-executable instructions corresponding to a sampling control logic stored on the machine-readable storage medium, the processor is caused to perform the sampling method of the scanning device of claim 4.

7. The apparatus according to claim 6, wherein, when setting a lower threshold and an upper threshold of the ray attenuation variation at the scanning angle, the machine-executable instructions cause the processor to:
construct an attenuation value difference group with the respective first attenuation value differences for the plurality of channels and the respective second attenuation value differences for the plurality of channels;
select a minimum value from the attenuation value difference group as the lower threshold of the ray attenuation variation at the scanning angle; and
select a maximum value from the attenuation value difference group as the upper threshold of the ray attenuation variation at the scanning angle.

8. A sampling apparatus of a scanning device, the device comprising:
a processor and a machine-readable storage medium,
wherein by invoking and executing machine-executable instructions corresponding to a sampling control logic stored on the machine-readable storage medium, the processor is caused to:
acquire a ray attenuation variation at each of a plurality of scanning angles of the scanning device;
determine a corrected sampling interval at each of the scanning angles of the scanning device by adjusting an initial sampling interval at each of the scanning angles of the scanning device according to the ray attenuation variation at each of the scanning angles; and
perform actual sampling on a subject according to the corrected sampling interval at each of the scanning angles of the scanning device;
wherein when acquiring the ray attenuation variation at each of the plurality of scanning angles of the scanning device, the machine-executable instructions cause the processor to:
determine an attenuation value of a scanning ray at each of the scanning angles; and
determine a ray attenuation variation at each of the scanning angles according to the attenuation value of the scanning ray at each of the scanning angles;
wherein when determining the ray attenuation variation at each of the scanning angles according to the attenuation value of the scanning ray at each of the scanning angles, the machine-executable instructions cause the processor to:
take each of the scanning angles as an interested scanning angle;
take an attenuation value of the scanning ray at the interested scanning angle as a first attenuation value;
take an attenuation value of the scanning ray at a scanning angle immediately before the interested scanning angle as a second attenuation value;
take an attenuation value of scanning ray at a scanning angle immediately after the interested scanning angle as a third attenuation value;
determine an absolute value of a difference between the first attenuation value and the second attenuation value as a first attenuation value difference;
determine an absolute value of a difference between the first attenuation value and the third attenuation value as a second attenuation value difference; and
determine a sum of the first attenuation value difference and the second attenuation value difference as the ray attenuation variation at the interested scanning angle.

9. The apparatus according to claim 8, wherein, when adjusting the initial sampling interval at the scanning angle of the scanning device, the machine-executable instructions cause the processor to:
set a lower threshold and an upper threshold of the ray attenuation variation at the scanning angle;
increase the initial sampling interval at the scanning angle of the scanning device when the ray attenuation variation at the scanning angle is smaller than the lower threshold;
decrease the initial sampling interval at the scanning angle of the scanning device when the ray attenuation variation at the scanning angle is greater than the upper threshold; and
maintain the initial sampling interval at the scanning angle of the scanning device unchanged when the ray attenuation variation at the scanning angle is between the lower threshold and the upper threshold.

10. The apparatus according to claim 9, wherein the machine-executable instructions further cause the processor to:
determine each of the scanning angles in a first circle of a scanning process for the scanning device by performing a pre-scanning on the subject with the scanning device;
determine the ray attenuation variation at each of the scanning angles in the first circle of the scanning process;
determine the corrected sampling interval at each of the scanning angles of the scanning device in the first circle of the scanning process by adjusting the initial sampling interval at each of the scanning angles of the scanning device in the first circle of scanning process according to the ray attenuation variation at each of the scanning angles in the first circle of the scanning process;
construct a fixed sampling scheme of the scanning device with the corrected sampling interval at each of the scanning angles of the scanning device in the first circle of the scanning process; and
perform the actual sampling on the subject according to the fixed sampling scheme in each circle of the scanning process of the scanning device.

* * * * *